US011767314B2

(12) United States Patent
Au et al.

(10) Patent No.: US 11,767,314 B2
(45) Date of Patent: Sep. 26, 2023

(54) BIOENERGETIC NICOTINIC ACID GLYCEROL ESTERS, COMPOSITIONS AND METHODS OF USING SAME

(71) Applicant: Conopco, Inc., Englewood Cliffs, NJ (US)

(72) Inventors: Van Au, Oxford, CT (US); Bijan Harichian, Irvine, CA (US); John Chun-Sing Nip, Shelton, CT (US); Jose Guillermo Rosa, Cheshire, CT (US)

(73) Assignee: CONOPCO, INC., Englewood Cliffs, NJ (US)

( * ) Notice: Subject to any disclaimer, the term of this patent is extended or adjusted under 35 U.S.C. 154(b) by 349 days.

(21) Appl. No.: 17/288,173

(22) PCT Filed: Oct. 29, 2019

(86) PCT No.: PCT/EP2019/079543
§ 371 (c)(1),
(2) Date: Apr. 23, 2021

(87) PCT Pub. No.: WO2020/089236
PCT Pub. Date: May 7, 2020

(65) Prior Publication Data

US 2021/0380564 A1 Dec. 9, 2021

(30) Foreign Application Priority Data

Nov. 2, 2018 (EP) .................................... 18204203

(51) Int. Cl.

| | |
|---|---|
| ***C07D 405/12*** | (2006.01) |
| ***A61K 8/06*** | (2006.01) |
| ***A61K 8/49*** | (2006.01) |
| ***A61Q 19/08*** | (2006.01) |
| ***C07D 213/80*** | (2006.01) |

(52) U.S. Cl.
CPC ............ *C07D 405/12* (2013.01); *A61K 8/062* (2013.01); *A61K 8/4926* (2013.01); *A61Q 19/08* (2013.01); *C07D 213/80* (2013.01)

(58) Field of Classification Search
CPC ............................ A61K 8/4926; C07D 213/80
See application file for complete search history.

(56) References Cited

U.S. PATENT DOCUMENTS

| | | | |
|---|---|---|---|
| 4,329,338 | A | 5/1982 | Szego et al. |
| 5,385,920 | A | 1/1995 | Cordi et al. |
| 5,833,998 | A | 10/1998 | Biedermann et al. |
| 5,939,082 | A | 8/1999 | Oblong et al. |
| 6,217,888 | B1 | 4/2001 | Oblong et al. |
| 6,238,678 | B1 | 5/2001 | Oblong et al. |
| 6,403,619 | B1 | 6/2002 | Jacobson et al. |
| 6,677,361 | B2 | 1/2004 | Jacobson et al. |
| 8,741,357 | B2 | 6/2014 | Lintner et al. |
| 9,181,189 | B2 | 11/2015 | Redoules et al. |
| 2002/0025926 | A1 | 2/2002 | Hebert |
| 2002/0032169 | A1 | 3/2002 | Henderson et al. |
| 2002/0119950 | A1 | 8/2002 | Henderson et al. |
| 2003/0198656 | A1 | 10/2003 | Yu et al. |
| 2004/0047896 | A1 | 3/2004 | Malnoe et al. |
| 2004/0213819 | A1 | 10/2004 | Albrecht |
| 2005/0249826 | A1 | 11/2005 | Smola et al. |
| 2006/0083796 | A1 | 4/2006 | Pridmore-Merten et al. |
| 2007/0110731 | A1 | 5/2007 | Riley |
| 2007/0116696 | A1 | 5/2007 | Riley |
| 2008/0206169 | A1 | 8/2008 | Millikin et al. |
| 2008/0305094 | A1 | 12/2008 | Pridmore-Merten |
| 2009/0017147 | A1 | 1/2009 | Lintner |
| 2009/0214607 | A1 | 8/2009 | Lintner et al. |
| 2011/0053990 | A1 | 3/2011 | Milne et al. |
| 2011/0253933 | A1 | 10/2011 | Hirata et al. |
| 2012/0070394 | A1 | 3/2012 | Sequin |
| 2012/0141387 | A1 | 6/2012 | Msika et al. |
| 2012/0183600 | A1 | 7/2012 | Chen |
| 2012/0252850 | A1 | 10/2012 | Milne et al. |
| 2012/0264791 | A1 | 10/2012 | Milne |
| 2014/0315950 | A1 | 10/2014 | Redoules et al. |
| 2018/0071273 | A1 | 3/2018 | Horu |

FOREIGN PATENT DOCUMENTS

| | | |
|---|---|---|
| BE | 881494 | 8/1980 |
| CH | 695414 | 5/2006 |
| DE | 10259966 | 7/2004 |

(Continued)

OTHER PUBLICATIONS

Search report and Written Opinion in EP18204203; dated Jan. 16, 2019.
Search Report and Written Opinion in PCTEP2019079543; dated Jan. 21, 2020.
Written Opinion 2 in PCTEP2019079543; dated Oct. 19, 2020.
Revitalizing Day Cream Record ID 179574; Mintel GNPD; May 2012; pp. 1-4.
Eye cream Record ID 1795426; MINTEL GNPD; May 2012; pp. 1-5.
Anti-Hair Loss gel record ID 1086719; Mintel GNPD; May 2009; pp. 1-3.
Anti-Hair Loss Shampoo record ID 1086736; Mintel GNDP; May 2009; pp. 1-2.
Liu, et al.; Nicotinamide prevents NAD+ depletion and protects neurons against excitotoxicity and cerebral ischemia: NAD+ consumption by SIRT1 may endanger energetically compromised neurons; Neuromolecular medicine, 2009; pp. 28-42; 11(1).

(Continued)

*Primary Examiner* — Andrew S Rosenthal
(74) *Attorney, Agent, or Firm* — Stephanie S. DelPonte

(57) ABSTRACT

New nicotinic acid glycerol ester compound(s) (NAEs); topical personal care compositions containing NAEs; and methods for modulating or activating cellular AMPK levels; and for increasing skin cellular bioenergetics are described. Use of one or more of the nicotinic acid glycerol ester compounds for modulating or activating cellular AMPK levels; and for increasing skin cellular bioenergetics are described. Use of a skin benefit agent comprising certain nicotinic acid glycerol ester compounds in the manufacture of a topical personal care composition for modulating or activating cellular AMPK levels; and for increasing skin cellular bioenergetics are described.

14 Claims, No Drawings

(56) References Cited

FOREIGN PATENT DOCUMENTS

| | | |
|---|---|---|
| EP | 0574312 | 12/1993 |
| EP | 1762247 | 3/2007 |
| ES | 380233 | 8/1972 |
| GB | 2210789 | 6/1989 |
| IN | 00052CH2010 | 5/2012 |
| JP | 511624 | 1/1976 |
| JP | 2012206942 | 10/2012 |
| KR | 1020140140872 | 12/2014 |
| WO | WO9739733 | 10/1997 |
| WO | WO9848816 | 11/1998 |
| WO | WO9947114 | 9/1999 |
| WO | WO9947141 | 9/1999 |
| WO | WO0040217 | 7/2000 |
| WO | WO02071874 | 9/2002 |
| WO | WO2004024108 | 3/2004 |
| WO | WO2004026287 | 4/2004 |
| WO | WO2004000042 | 5/2004 |
| WO | WO2005074719 | 8/2005 |
| WO | WO2006075311 | 7/2006 |
| WO | WO2006120646 | 11/2006 |
| WO | WO2008025755 | 3/2008 |
| WO | WO2008057423 | 5/2008 |
| WO | WO2011018501 | 2/2011 |
| WO | WO2012027827 | 3/2012 |
| WO | WO2012035685 | 3/2012 |
| WO | WO2013083825 | 6/2013 |
| WO | WO2017015660 | 1/2017 |
| WO | WO2017062311 | 4/2017 |

OTHER PUBLICATIONS

Maiese, et al.; The vitamin nicotinamide: translating nutrition into clinical care; Molecules; Sep. 2009; pp. 3446-3485; 14(9).
Sivapirabu, et al.; Topical nicotinamide modulates cellular energy metabolism and provides broad-spectrum protection against ultraviolet radiation-induced immunosuppression in humans; The British journal of dermatology; 2009; pp. 1357-1364; 161(6).
Surjana et al.; Nicotinamide in dermatology and photoprotection; Skinmed; 2011; pp. 360-365; 9(6).
Chen, et al.; Nicotinamide and the skin; The Australasian journal of dermatology; 2014; pp. 169-175; 55(3).
Goodge, et al.; Effects of n-1 alkyl nicotinamide chlorides on nadh oxidation in rat liver sub mitochondrial particles; Archives of Biochemistry and Biophysics; 1970; pp. 190-196; 140(1).
IPRP2 in PCTEP2019079543; dated Feb. 10, 2021.
Supple Preparation facial toner Record ID 5626949; Mintel GNDP; 2018; pp. 1-4.
Rich Moist Soothing Cream Record ID 5520501; Mintel GNDP; 2018; pp. 1-4.
Strengthening Base Treatment Record ID 5359465; Mintel GNPD; 2018; pp. 1-3.
9 in 1 Base nail treatment Record ID 5145261; Mintel GNPD; 2017; pp. 1-3.
Nail Essentials Set Record ID 5075929; Mintel GNPD; 2017; pp. 1-6.
Nail hardener Record ID 5054913; Mintel GNPD; 2017; pp. 1-4.
All in One Nail Care record ID 4784777; Mintel GNPD; 2017; p. 1-3.
ANX 10 Total Repair Liquid Diamond Nail Conditioner Record ID 4656703; Mintel GNPD; 2017; pp. 1-4.
7 in Saviour Record ID 4368013; Mintel GNPD; 2016; pp. 1-4.
Nail Growth treatment Record ID 4254317; Mintel GNPD; 2016; pp. 1-4.
Oxygen Treatment Record ID 4260437; Mintel GNPD; 2016; pp. 1-4.
Total Action 8 in 1 Nail Polish remover, Reocrd ID 4207709; Mintel GNPD; 2016; pp. 1-3.
Bio-Excellence eyelach & eyebrwo enhancing serum record ID 4094761; Mintel GNPD; 2016; pp. 1-4.
Extra strong nail hardener record ID 3826175; mintel GNPD; 2016; pp. 1-4.
Total Action 8in1 Nail Polish Remover Record ID 3790951; Minte GNPD; 2016; pp. 1-3.
Mask Record ID 3575207; Mintel GNPD; 2015; pp. 1-2.
7 in 1 Saviour Record ID 3152859; Mintel GNPD; 2015; pp. 1-4.
Set Record ID 3182533; Mintel GNPD; 2015; pp. 1-5.
7 in 1 Saviour Record ID 2258938; Mintel GNPD; 2013; pp. 1-4.
Repair Care with Rose Oil Record 10170732; Mintel GNPD; 2004; pp. 1-2.
Nail Polish Remover Record ID 1172982; Mintel GNPD; 2009; pp. 1-3.
Gift Set Record ID 1195336; Mintel GNPD; 2009; pp. 1-3.
Aminoceutical Mask Record ID 1911140; Mintel GNPD; 2012; pp. 1-3.
Hey Mr. Lash Care Record ID 1946689; Mintel GNPD; 2012; pp. 1-3.
Serum Record ID 1998256; Mintel GNPD; 2013; pp. 1-3.
Serum Record ID 2080577; Mintel GNPD; 2013; pp. 1-3.
7 in 1 Saviour Record ID 2089257; Mintel GNPD; 2013; pp. 1-4.
Miracle Repair 7 7-in1 Multi Active Care record ID 2105062; Mintel GNPD; 2013; pp. 1-3.
Miracle Repair 7-in-1 Multi Active Care Serum record ID 2078050; Mintel GNPD; 2013; pp. 1-4.
7 in 1 Saviour Record ID 2126996; Mintel GNPD; 2013; pp. 1-4.
7 in 1 Saviour Record ID 2144818; Mintel GNDP; 2013; pp. 1-3.
7 in 1 Saviour Record ID 2083650; Mintel GNPD; 2013; pp. 1-4.
7 in 1 Saviour record ID 2223175; Mintel GNPD; 2013; pp. 1-4.
Serum Record ID 2245467; Mintel GNPD; 2013; pp. 1-3.
Nail Hardener Record ID 2258947; Mintel GNPD; 2013; pp. 1-4.
STN Registry database, CAS No. 58920-63-1, 1 page (1984).

BIOENERGETIC NICOTINIC ACID GLYCEROL ESTERS, COMPOSITIONS AND METHODS OF USING SAME

FIELD OF THE INVENTION

Nicotinic acid glycerol esters, topical compositions containing same, as well as methods of upregulating AMPK metabolite levels within skin cells and increasing skin cellular energy or skin bioenergetics.

BACKGROUND OF THE INVENTION

High energy is generally associated with desirable attributes such as vigor, health, youth. What is less evident is whether or how high energy or the associated attributes can be achieved, and particularly whether or how they can be achieved on a cellular level.

While there is much literature on the cellular metabolic energy cycle, the art of leveraging its components (metabolites) or component steps to achieve youth or its perception via appearance remains uncertain. While true in all cells of the body, it is particularly unpredictable whether or how the cellular energy metabolic cycle or its manipulation can achieve youthful looking skin.

A master cellular energy regulator is AMP-activated protein kinase (AMPK). AMPK controls energy consuming (anabolic) and energy producing (catabolic) processes. AMPK maintains energy homeostasis at the cellular level by switching between anabolic and catabolic processes. Specifically, in response to change in cellular energy state, where there is a decrease in ATP level with an increase in AMP level, AMPK becomes activated by allosteric binding of AMP. The activated AMPK prevents further reduction in ATP by blocking ATP consuming processes while promoting ATP producing ones. See Graeme J. Gowans et al. entitled "*AMP Is a True Physiological Regulator of AMP-Activated Protein Kinase by Both Allosteric Activation and Enhancing Net Phosphorylation*", Cell Metabolism 18, P. 556-566, 2013. The homeostasis may be illustrated as part of the cellular metabolic pathway as a relative balance among metabolites:

AMPK→←AMP→←ADP→←ATP where

AMPK (5' adenosine monophosphate-activated protein kinase)

AMP (adenosine monophosphate)

ADP (adenosine diphosphate)

ATP (adenosine triphosphate)

It can be seen, therefore, that low ATP or high AMP level or concentration within the cell shifts the equilibrium to turn on AMPK, which in turn phosphorylates AMP back to ATP (associated with high energy). Stated otherwise, increasing the AMP/ATP ratio and/or increasing AMPK levels leads to higher bioenergetic state within cells, including human skin cells.

Without wishing to be bound by theory, Applicants believe that compounds that modulate AMPK levels contribute to increase in cellular energy. Boosting amounts of such compounds in skin cells is associated with skin benefits.

When consumers wish to look younger by reducing facial lines, wrinkles, and blotchy color marks on the skin, they find it desirable to deliver skin benefits via methods that rely on the application of topical compositions. Active ingredients for incorporation in topical compositions, which can deliver consumer skin benefits are always sought. There is an ongoing need for active ingredients for incorporation in topical compositions, which active ingredients deliver skin benefits by modulating metabolites in the skin cell energy cycle, thereby providing energy to skin cells.

This invention, therefore, is directed to compounds active to modulate the cell energy cycle, compositions containing the active compounds, and that have been boosted with an optional skin benefit agent, as well as methods of increasing the bioenergetics on a cellular level. The composition of the present invention can be topically applied without causing skin irritation, while simultaneously delivering excellent skin benefits. The inventive compounds and composition facilitate delivery of actives for enhanced solubilization and efficacy.

ADDITIONAL INFORMATION

Certain nicotinates as lipogenesis inhibitors are disclosed in U.S. Pat. No. 5,385,920. Nicotinyl esters (e.g. including myristyl nicotinate) have been disclosed for lowering serum triglyceride, via topical delivery into the bloodstream, in U.S. Pat. No. 6,677,361. However, myristyl nicotinate is a very lipophilic (greasy) molecule, having a high log P, so it is water insoluble and difficult to formulate as a skin benefit agent in a topical cosmetic composition.

Efforts have been disclosed for making formulations to treat skin. In U.S. Pat. No. 6,333,065, pharmaceutical compositions comprising agents, some including $C_1$ to $C_{30}$ Hydrocarbon chain nicotinic acid esters, to treat disorders such as sunburn and other skin deterioration that results from DNA damage in skin cells are described.

Still other efforts have been disclosed for making formulations to treat skin. Certain nicotinates are disclosed as treatment for acne and seborrheic dermatitis in US2014/0315950.

Generally, delivery or bioavailability of nicotinic acid esters, particularly esters containing saturated long chain hydrocarbon chains, from topical compositions is challenging due to their extremely low solubility in biologically acceptable vehicle.

Nicotinic acid, also known as niacin, causes skin irritation when applied topically. An alternative is niacinamide or Vitamin B3, however, nicotinic acid precursors with even better activity, delivery, and/or solubility are sought. For example, nicotinic acid esters with optimized physicochemical properties, allowing efficient (or controlled release) partitioning from formulation into the skin matrix, delivery through the upper skin layers into the sub-dermal layers and subsequent release of nicotinic acid (thereby minimizing skin irritation) would be ideal for skin applications.

None of the additional information above discloses AMPK mechanism or describes a composition with nicotinic acid precursors that activate AMPK, increase AMP/ATP ratio, provide bioenergetics effects, when topically applied to the skin in a cosmetically suitable carrier.

SUMMARY OF THE INVENTION

The present invention overcomes the prior art deficiencies by providing a new nicotinic acid glycerol ester compound(s) (NAEs); topical personal care compositions containing certain NAEs and methods for modulating cellular AMPK levels; and a topical personal care composition with solubilized nicotinic acid glycerol esters in a suitable vehicle for increasing skin cellular bioenergetics. The nicotinic acid glycerol esters with bioenergetics skin effects according to the present invention contain a glycerol moiety and a relatively short chain hydrocarbon moiety, which allow for better partitioning and delivery of the compound(s) through skin and controlled release of nicotinic acid for maximum efficacy and minimum skin irritancy.

Without wishing to be bound by theory, Applicants believe that compounds that modulate AMPK contribute to increase in cellular energy. Activating AMPK, thereby boosting amounts of its metabolites in skin cells is associated with skin benefits. AMPK or its metabolites such as AMP and ATP may be used as biomarkers for avoiding skin aging and/or for boosting skin cellular energy.

The present invention is based on discovery of active ingredients for incorporation in topical compositions, which can deliver consumer skin benefits by increasing AMP/ATP levels and boosting AMPK in skin cells.

In a first aspect, a nicotinic acid glycerol ester compound or mixture of compounds is shown below and referred to as compounds of Structural Formula I, Structural Formula II, Structural Formula III, and Structural Formula IV. One or more nicotinic acid glycerol ester compound(s) is selected from the group consisting of:

(a) Structural Formula IV

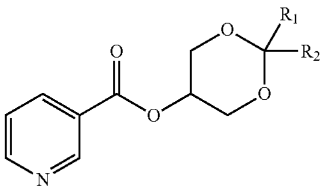

wherein $R_1$ and $R_2$ are independently $C_1$-$C_5$ linear, branched or cyclic alkyl; saturated or unsaturated; with or without a heteroatom; including salts thereof;

(b) Optionally, Structural Formula I

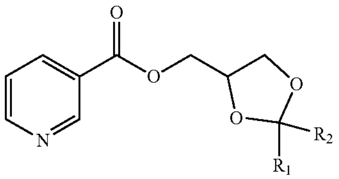

wherein $R_1$ and $R_2$ are independently $C_1$-$C_5$ linear, branched or cyclic alkyl; saturated or unsaturated; with or without a heteroatom (like —OH); including salts thereof;

(c) Optionally, Structural Formula II

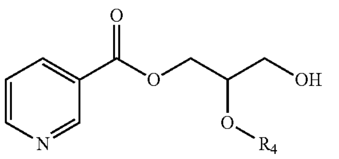

wherein $R_4$ is H or O═C—X2, where X2=$C_1$-$C_{11}$ linear, branched or cyclic alkyl; saturated or unsaturated; with or without a heteroatom (like —OH); including salts thereof, (d) Optionally, Structural Formula III

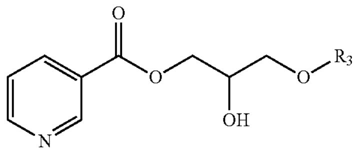

Wherein $R_3$ is H or O═C—X (glycerol ester), where X═$C_1$-$C_{12}$ linear, branched or cyclic alkyl; saturated or unsaturated; with or without a heteroatom (like —OH); including salts thereof; and (e) mixtures thereof in any combination with compound of Structural Formula IV, or derivatives thereof.

In a second aspect, the present invention is a personal care composition comprising compounds Structural Formula I, Structural Formula II, Structural Formula III, Structural Formula IV, and mixtures of any combination thereof.

In a third aspect, the present invention is the use of a nicotinic acid glycerol ester and/or derivative thereof for ameliorating signs of aging, wherein said nicotinic acid precursor comprises one or more of the selected NAE compounds and mixtures thereof in a composition.

In a fourth aspect, the present invention is the use of a nicotinic acid glycerol ester in the manufacture of a topical personal care composition for modulating cellular AMPK levels.

Structural Formula I

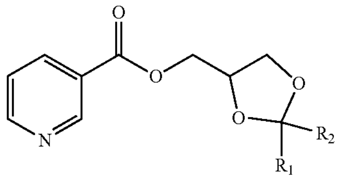

In which, $R_1$ and $R_2$ are separate groups or combined together to form a ring. In a preferred embodiment $R_1$ and $R_2$ are independently $C_1$-$C_5$ linear, branched or cyclic alkyl; saturated or unsaturated; with or without a heteroatom (like —OH); including salts thereof.

The glycerol moiety and the relatively short carbon chains on the R-groups are designed to enhance solubility and control the level of water-to-oil partitioning in a cosmetic composition, thereby optimizing delivery of the compound(s) onto and throughout the distinct layers of skin.

Structural Formula II

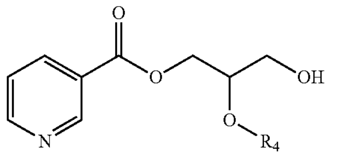

In which $R_4$ is H or O═C—X2, where X2=$C_1$-$C_{11}$ linear, branched or cyclic alkyl; saturated or unsaturated; with or without a heteroatom (like —OH); including salts thereof. Preferably, $R_4$ is H.

Where log P is understood to be a measure of whether a molecule is relatively lipophilic (when log P is higher) or relatively hydrophilic (when log P is lower), Compounds of structural formula II have a Calculated log P<about 5.8 and are relatively soluble compounds.

Additionally, compounds of Structural Formula II are Nicotinate linked glycerols, so that each compound provides additional benefits, such as moisturization, upon delivery through the skin.

Structural Formula III

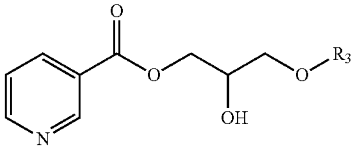

In which $R_3$ is H or O═C—X (glycerol ester), where X═$C_1$-$C_{12}$ linear, branched or cyclic alkyl; saturated or unsaturated; with or without a heteroatom (like —OH); including salts thereof. Preferably, X═$C_1$-$C_{11}$ linear, branched or cyclic alkyl; more preferably $C_{11}$ alkyl.

Compounds of structural formula III have a Calculated log P<about 5.8 and are relatively soluble compounds.

Structural Formula IV

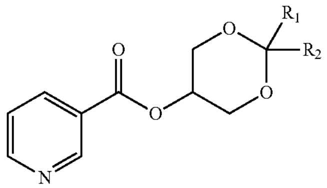

In which $R_1$ and $R_2$ are separate groups or are combined together to form a ring; and $R_1$ and $R_2$ are independently $C_1$-$C_5$ linear, branched or cyclic alkyl; saturated or unsaturated; with or without a heteroatom (like —OH); including salts thereof.

Preferably, $R_1$ and $R_2$ are independently $C_1$. More preferably, both $R_1$ and $R_2$ are $C_1$.

Compounds of structural formula IV are new. Compounds of structural formula IV have a Calculated Log P<about 5.8 and are relatively soluble compounds.

Preferred examples of the nicotinic acid glycerol esters that may be used in this invention include those represented by the formula shown in the Table below and referred to as VC1, VC2, VC3, VC4, and VC5.

TABLE 1

| | Structure | Chemical Names |
|---|---|---|
| VC1 | 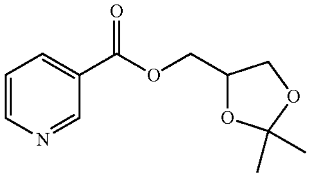 [SMILES: CC1(C)OCC(COC(=O)c2cccnc2)O1] | (2,2-dimethyl-1,3-dioxolan-4-yl)methyl nicotinate (Structural Formula I Compound where each $R_1$, $R_2$ is $C_1$) |
| VC2 | 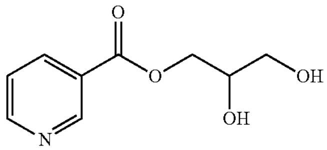 [SMILES: O=C(OCC(O)CO)c1cccnc1] | 2,3-dihydroxypropyl nicotinate Or Glycerylmono-nicotinate |
| VC3 | 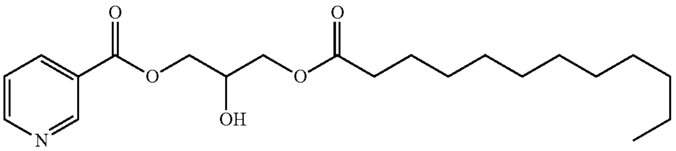 [SMILES: CCCCCCCCCCCC(=O)OCC(O)COC(=O)c1cccnc1] | 3-(dodecanoyloxy)-2-hydroxypropyl nicotinate |
| VC4 | 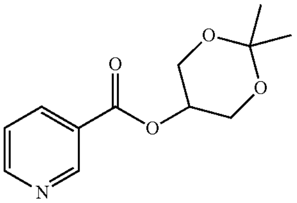 [SMILES: CC1(C)OCC(OC(=O)c2cccnc2)CO1] | 2,2-dimethyl-1,3-dioxan-5-yl nicotinate |
| VC5 | | 1,3-dihydroxypropyl-2-nicotinate |

According to one embodiment, one or more nicotinic acid glycerol ester compound(s) is selected from the group consisting of:

(a) Structural Formula IV;

(b) Optionally, Structural Formula I, Structural Formula II, Structural Formula III; and (c) mixtures thereof.

In another embodiment, the present invention is the use of a nicotinic acid glycerol esters and/or derivatives thereof for ameliorating signs of aging, wherein said nicotinic acid glycerol ester comprises one or more compounds selected from the group consisting of Structural Formula I, Structural Formula II, Structural Formula III, Structural Formula IV, and mixtures thereof in a composition.

Also required characteristics for formulation and delivery are water solubility and the ability to control the compound's partitioning between water and oil matrices. Nicotinic acid glycerol ester compounds are selected according to the present invention with a glycerol moiety and with suitable hydrocarbon chain length to achieve the right hydrophilic-lipophilic balance and ultimately optimize the compound's solubility and suitability in various compositions. Hydrocarbon chains that are too long and have a high Log P are avoided since these limit the compound's solubility profile and delivery properties onto and throughout the skin.

Nicotinic acid glycerol esters according to the present invention are selected for suitable hydrophilic and lipophilic balance, with calculated log P between log P<5.8 and Log P>−1.

Compounds VC1, VC2 and VC4 are preferred for their enhanced water solubility and relatively small molecular size, which also improves dermal delivery.

Additionally, Compounds VC2 and VC3 are preferred as glycerol precursors, so that they provide additional benefits, such as moisturization, upon delivery through the skin, and via hydrolysis from skin esterases.

Further, Compound VC3 is a more lipophilic derivative of VC2, thereby offering sustained/controlled release delivery modalities from formulation and through the skin.

Advantageously, the nicotinic acid glycerol ester compounds of the present invention are AMPK activators. VC1, VC2 and VC4 are most preferred as having demonstrably increased AMP/ATP ratio.

Salt Forms

All compounds according to the present invention (Structures I-IV and VC1-4 and any derivatives thereof) have a nitrogen atom on the ring (pyridine ring) available to accept a proton and form a salt with a variety of counterions ($X^-$) as shown below:

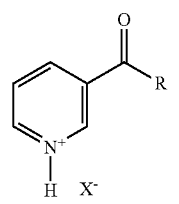

Counterions can be selected from chloride, bromide, iodide, hydroxide, sulfate, sulfonate, nitrate, phosphate, formate, tartrate, lactate, oxalate, fumarate, maleate, succinate, malonate, citrate or $R_5CO_2^-$ where $R_5$ is a $C_1$-$C_{22}$ alkyl group, which may be linear, branched or cyclic, saturated or unsaturated, and substituted with one or more heteroatoms selected from O, S.

Composition

In a second embodiment, the present invention is directed to a composition comprising:

(a) a nicotinic acid ester glycerol compound selected from the group consisting of Structural Formula I, Structural Formula II, Structural Formula III, Structural Formula IV, and mixtures of any two or more thereof;
and (b) a cosmetically acceptable carrier.

In a preferred embodiment, the present invention is directed to a composition comprising:

(b) a nicotinic acid ester selected from the group consisting of VC1, VC2, VC3, VC4, and mixtures of any two or more thereof;
and (b) a cosmetically acceptable carrier.

In a third embodiment, the present invention is directed to a method of increasing AMPK activity by topically applying compositions containing one or more of the nicotinic acid glycerol esters according to the present invention.

In a fourth embodiment, the present invention is directed to use of the nicotinic acid glycerol esters and compositions containing same to increase skin cellular energy and/or boost AMPK or AMP/ATP ratio, and/or serve as a skin benefit agent against signs of aging.

All other aspects of the present invention will readily become apparent upon considering the detailed description and examples which follow.

Throughout the specification and claims, the following terms take the meanings explicitly associated herein, unless the context clearly dictates otherwise.

The phrases "in one embodiment" and "in some embodiments" as used herein do not necessarily refer to the same embodiment(s), though it may. Furthermore, the phrases "in another embodiment" and "in some other embodiments" as used herein do not necessarily refer to a different embodiment, although it may. Thus, as described below, various embodiments of the invention may be readily combined, without departing from the scope or spirit of the invention. In addition, each of the examples given in connection with the various embodiments of the invention which are intended to be illustrative, and not restrictive.

Skin, as used herein, is meant to include skin on the feet, face, neck, chest, back, arms, hands, legs, buttocks and scalp (including hair). The composition of this invention includes creams, lotions, balms, serums, deodorants and antiperspirants, shampoos, conditioners, bars and liquid wash products. In a preferred embodiment, the composition of this invention is a leave-on composition like a leave-on cream or lotion.

Unless explicitly stated otherwise, all ranges described herein are meant to include all ranges subsumed therein.

Except in the examples, or where otherwise explicitly indicated, all numbers in this description indicating amounts of material or conditions of reaction, physical properties of materials and/or use are to be understood as modified by the word "about." All amounts are by weight of the final composition, unless otherwise specified. The disclosure of the invention as found herein is to be considered to cover all embodiments as found in the claims as being multiply dependent upon each other irrespective of the fact that claims may be found without multiple dependency or redundancy. In specifying any range of concentration or amount, any particular upper concentration can be associated with any particular lower concentration or amount.

"Comprising" is intended to mean "including" but not necessarily "consisting of" or "composed of." In other words, the listed steps or options need not be exhaustive. The term comprises is meant to encompass the terms consisting essentially of and consisting of.

"Derivative(s)" refers to compounds naturally or artificially derived from the selected nicotinic acid glycerol esters according to the present invention, including salt forms.

"Leave-on composition" refers to a composition that is applied to the skin and is not intended to be washed or rinsed off for some period of time, specifically hours, as contrasted with skin cleansing or wash-off or rinse-off compositions which are rinsed off or washed off immediately or minutes after the application.

"Modulating" or "activating" refer to their ordinary dictionary meaning, and include upregulating as it relates to cellular metabolite levels including AMPK levels.

"Personal care composition" refers to any product applied to a human body for improving appearance, sun protection, cleansing, odor control, moisturization or general aesthetics. Non-limiting examples of personal care compositions include skin lotions, creams, gels, lotions, facial masks, sticks, shampoos, conditioners, shower gels, toilet bars, antiperspirants, deodorants, shave creams, depilatories, lipsticks, foundations, mascara, sunless tanners and sunscreen lotions.

"Skin cosmetic composition" refers to any product applied to a human body for improving appearance, sun protection, reducing wrinkled appearance or other signs of photoaging, odor control, skin lightening, even skin tone, or general aesthetics. The composition of the invention which is suitable to provide benefit(s) to skin can be an emulsion or a composition that is free of water and emulsifier. Non-limiting examples of topical cosmetic skin compositions include skin lotions, creams, facial masks, gels, sticks, antiperspirants, deodorants, lipsticks, foundations, mascara, liquid or gel body washes, soap bars, sunless tanners and sunscreen lotions.

DETAILED DESCRIPTION OF THE INVENTION

The present invention is directed to selected nicotinic acid glycerol ester compounds, topical compositions containing the same, methods for using the compounds and compositions as bioenergetics skin benefit agents by topically applying to the skin. More particularly, the invention is directed to selected nicotinic acid glycerol ester compounds, compositions using them as skin benefit agents alone and/or in combination to modulate the cellular metabolic energy cycle. The present invention is based on the finding that certain nicotinic acid glycerol esters when applied topically to the skin increase cellular AMP/ATP ratio, which results in an increase in AMPK activity. Increase in AMPK activity is associated with efficient use of energy, control of glucose and lipid metabolism, increase of cellular repair/rejuvenation, decrease in senescence cells, increase of anti-oxidant defense, and reduction of inflammation. The personal care benefits of applying a cosmetic composition containing the selected nicotinic acid glycerol esters include, without limitation, anti-ageing, anti-inflammation, and anti-stress (including UV and pollution stresses).

In a first aspect, the present invention is directed to a nicotinic acid ester compound or mixture of compounds shown below and referred to as compounds of Structural Formula I, Structural Formula II, Structural Formula III, and Structural Formula IV.

In a second aspect, the present invention is directed to a composition comprising:

(a) a nicotinic acid ester compound selected from the group consisting of Structural Formula I, Structural Formula II, Structural Formula III, Structural Formula IV, and mixtures of any two or more thereof;
and (b) a cosmetically acceptable carrier.

In a third aspect, the present invention is the use of a nicotinic acid glycerol ester and/or derivative thereof for ameliorating signs of aging, wherein said nicotinic acid precursor comprises one or more of the selected NAE compounds and mixtures thereof in a composition.

In a fourth aspect, the present invention is the use of a nicotinic acid glycerol ester in the manufacture of a topical personal care composition for modulating cellular AMPK levels.

Structural Formula I

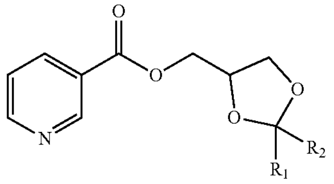

In which, $R_1$ and $R_2$ are separate groups or combined together to form a ring. In a preferred embodiment $R_1$ and $R_2$ are independently $C_1$-$C_5$ linear, branched or cyclic alkyl; saturated or unsaturated; with or without a heteroatom (like —OH); including salts thereof.

The glycerol moiety and the relatively short carbon chains on the R-groups are designed to enhance solubility and control the level of water-to-oil partitioning in a cosmetic composition, thereby optimizing delivery of the compound (s) onto and throughout the distinct layers of skin.

Compounds according to the present invention, including compounds of Structural Formula I, have a log P (octanol-water partition coefficient, or a measure of the relative lipohilic-hydrophilic balance) of less than about 5.8 to increase partitioning from the formulation onto the skin and delivery through the upper skin layers well into the viable tissue. Preferably, log P of the inventive compounds is greater than about −1 and less than about 5.8.

Structural Formula II

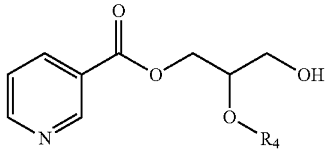

In which $R_4$ is H or O═C—X2, where X2=$C_1$-$C_{11}$ linear, branched or cyclic alkyl; saturated or unsaturated; with or without a heteroatom (like —OH); including salts thereof. Preferably, $R_4$ is H.

Where log P is understood to be a measure of whether a molecule is relatively lipophilic (when log P is higher) or relatively hydrophilic (when log P is lower), Compounds of structural formula II have a Calculated log P<about 5.8 and are relatively soluble compounds in water.

Additionally, compounds of Structural Formula II are Nicotinate linked glycerols, so that each compound provides additional benefits, such as, including but not limited to, moisturization, upon delivery through the skin.

Structural Formula III

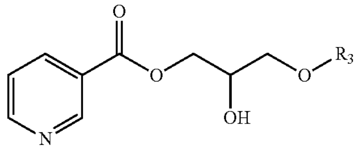

In which $R_3$ is H or O═C—X (glycerol ester) where X is $C_1$-$C_{12}$ linear, branched or cyclic alkyl; saturated or unsaturated; with or without a heteroatom (like —OH); including salts thereof. Preferably, X is $C_1$-$C_{11}$ linear, branched or cyclic alkyl; more preferably X is $C_{11}$ alkyl.

Compounds of structural formula III have a Calculated log P<about 5.8 and are q relatively soluble compounds in water.

Additionally, compounds of Structural Formula II are nicotinate linked glycerols and, unexpectedly, each compound provides additional benefits, such as, including but not limited to, moisturization, upon delivery through the skin.

Structural Formula IV

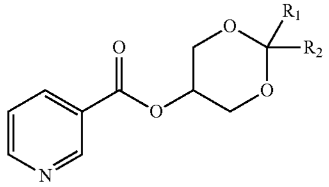

In which $R_1$ and $R_2$ are separate groups or combined together to form a ring; and $R_1$ and $R_2$ are independently $C_1$-$C_5$ linear, branched or cyclic alkyl; saturated or unsaturated; with or without a heteroatom (like —OH); including salts thereof. Preferably, $R_1$ and $R_2$ are independently $C_1$. More preferably, both $R_1$ and $R_2$ are $C_1$.

Compounds of structural formula IV are new. Compounds of structural formula IV have a Calculated log P<about 5.8 and are relatively soluble compounds in water.

Illustrative examples of the nicotinic acid esters that may be used in this invention include those represented by the formulas shown below and referred to as VC1, VC2, VC3, and VC4. The preferred NAEs used in this invention are compounds VC1, VC2, VC3, VC4, or a mixture thereof; more preferably VC4 as it is a new compound. Nicotinic acid glycerol ester compounds VC1, VC2 and VC4 are most preferred as AMPK activators, as they increased AMP/ATP ratio in testing.

NAEs according to the present invention are selected for suitable hydrophilic and lipophilic balance, with calculated log P between log P<5.8 and Log P>−1. Compounds VC1, VC2 and VC4 are preferred for their enhanced water solubility, having calculated Log P's of 1.45, −0.53 and 1.45, respectively.

NAE compound VC2 is preferred as a ready glycerol precursor which additionally has a moisturizing effect on the skin. In one preferred embodiment, a combination of compounds VC2 and VC3 is used for controlled delivery. Some immediate delivery is achieved with VC2 and some extended delivery is provided with VC3 as it has more prolonged delivery through the skin.

TABLE 2

| | Structure | Chemical Names |
|---|---|---|
| VC1 | 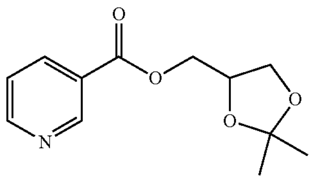 [SMILES: CC1(C)OCC(COC(=O)c2cccnc2)O1] | (2,2-dimethyl-1,3-dioxolan-4-yl)methyl nicotinate (Structural Formula I where $R_1$ and $R_2$ each represents a carbon chain of $C_1$) |
| VC2 | 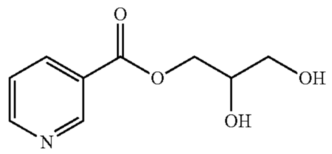 [SMILES: O=C(OCC(O)CO)c1cccnc1] | 2,3-dihydroxypropyl nicotinate Or Glycerylmononicotinate |
| VC3 | 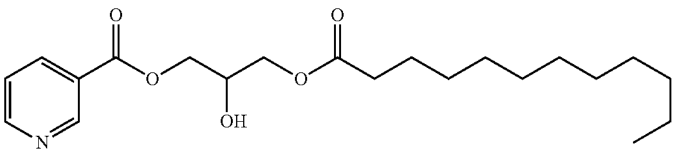 [SMILES: CCCCCCCCCCCC(=O)OCC(O)COC(=O)c1cccnc1] | 3-(dodecanoyloxy)-2-hydroxypropyl nicotinate |

TABLE 2-continued

| | Structure | Chemical Names |
|---|---|---|
| VC4 | 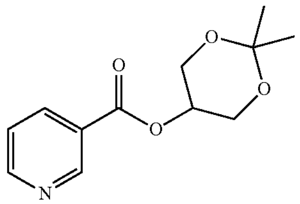 [SMILES: CC1(C)OCC(OC(=O)c2cccnc2)CO1] | 2,2-dimethyl-1,3-dioxan-5-yl nicotinate |
| VC5 | | 1,3-dihydroxypropyl-2-nicotinate |

Salts

Any of the nicotinic acid esters included in the present invention may be in the form of a salt or a salt thereof.

All compounds according to the present invention (Structures I-IV and VC1-4 and any other derivatives) have a nitrogen atom on the ring (pyridine ring) available to accept a proton and form a salt with a variety of counterions ($X^-$) as shown below:

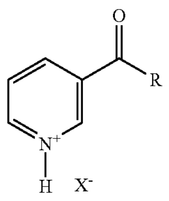

Counterions can be selected from chloride, bromide, iodide, hydroxide, sulfate, sulfonate, nitrate, phosphate, formate, tartrate, lactate, oxalate, fumarate, maleate, succinate, malonate, citrate or $R_5CO_2^-$ where $R_5$ is a $C_1$-$C_{22}$ alkyl group, which may be linear, branched or cyclic, saturated or unsaturated, and substituted with one or more heteroatoms selected from O, S.

Compositions

Even more preferably, the NAEs are used as part of a topical skin care composition which comprises compounds VC1, VC2, VC3, VC4, or a mixture thereof; more preferably VC1, VC2, VC4, or a mixture thereof as they are most water soluble, notably increase the AMP/ATP ratio and are AMKP activators.

Formulation of bioenergetics skin benefit agents is challenging and unpredictable. To be an effective bioenergetics skin benefit agent, a molecule has to penetrate the skin, reach the viable tissue and have sufficient solubility in water. Thus, water solubility is another required characteristic for formulation and delivery. A solubility parameter known as Log P, also known as octanol-water partition coefficient, is used to measure the relative lipophilic and hydrophilic balance. If Log P is too high (greater than about 6), a molecule will not penetrate well to the viable tissue of the skin. If Log P is too low, a molecule is too hydrophilic, and it partitions in water before it is able to penetrate the skin (e.g. sugars with too many —OH groups). NAEs according to the present invention are designed to have hydrophilic and lipophilic balance with calculated log P between log P<5.8 and Log P>−1. NAE compounds VC1, VC2 and VC4 are most water soluble; and VC3 is soluble but at lower concentrations.

Typically, the amount of nicotinic acid ester used in the compositions of this invention is from 0.001 to 10%, and preferably, from 0.01 to 6%, and most preferably, from 0.05 to 3.5%, based on total weight of the composition and including all ranges subsumed therein.

Process/Synthesis

The preferred NAEs used in this invention are VC1, VC2, VC3 and VC4. They are synthesized as follows, and their synthesis is representative of that for the corresponding compounds of Structural Formula I, II, II and IV:

Synthesis of VC1 [2,2-dimethyl-1,3-dioxolan-4-yl] methyl nicotinate]

Solketal [glycerol ketal chemical name] (2.5 g, 1 eq.) was dissolved in 50 ml chloroform and stirred at 0° C.

Triethylamine (3.84 g, 2 eq.) was added slowly to the solketal/chloroform solution over the course of five minutes. Nicotinoyl chloride HCl (3.36 g, 1 eq.) was added slowly over the course of 30 minutes. The reaction was stirred for 12 to 16 hours at room temperature of about 18° C. (64° F.) to about 20° C. (68° F.).

The reaction solution was diluted with 25 ml chloroform (bringing the total volume to 75 ml). The chloroform solution was washed with distilled water (75 ml), followed by 3% aqueous solution of sodium bicarbonate (75 ml), and then with distilled water. The organic layer was collected and dried over sodium sulfate. The sodium sulfate was filtered off via Hirsch filtration. The organic layer was concentrated under reduced pressure to give the crude product as a yellow oil.

The crude product was purified using flash chromatography with a mobile phase of 50:50 ethyl acetate:hexanes on silica column. Yield 3.238 g (72% yield)

Synthesis of VC2 [2,3-dihydroxypropyl nicotinate]

To form a solution, in a 50 ml round bottom flask with a reflux condenser were added: [2,2-dimethyl-1,3-dioxolan-4-yl] methyl nicotinate (961 mg)

and

20% glacial acetic acid (10 ml).

The solution was stirred and refluxed at about 100 C for about 6 hours. The solution was then placed on the rotovap. The solvent was removed under reduced pressure to give crude product (1.068 g).

Flash chromatography using ethyl acetate on silica column yielded 600 mg white solid (75.1% yield) product VC2.

VC2 is also available from Aurora Building Blocks, USA).

Synthesis of VC3 [3-(dodecanoyloxy)-2-hydroxypropyl nicotinate]

Dissolved in chloroform (30 ml) were:

1-lauroyl glycerol (0.5 g, 1 eq.) and triethylamine (0.374 g, 2 eq.), to which was added nicotinoyl chloride HCl (0.16 g, 1 eq.) to form a solution.

The solution was stirred at room temperature of about 18° C. (64° F.) to about 20° C. (68° F.) for about 48 hours. The solution was transferred to a separatory funnel and washed with distilled water, followed by 3% aqueous solution of sodium bicarbonate, and then with distilled water again. The chloroform layer was collected and dried over magnesium sulfate. The magnesium sulfate was filtered off via Hirsch filtration and rinsed with chloroform. The choroform layer was removed under reduced pressure to give the crude product (980 mg).

Flash chromatography with 60:40 ethyl acetate:hexane as eluent on silica gel column yielded VC3 product (310 mg, 55% yield).

Synthesis of VC4 [2,2-dimethyl-1,3-dioxan-5-yl] nicotinate]

A solution was formed by dissolving 1,3-O-Propylidene glycerol (500 mg, 1 eq.) in chloroform (10 ml) and stirring at 0° C. DMAP (924.4 mg, 2 eq.) was added slowly to the solution over the course of about five minutes. Nicotinoyl chloride HCl (673.5 mg, 1 eq.) was added slowly. The reaction was stirred overnight (for about 12-16 hours) at room temperature of about 18° C. (64° F.) to about 20° C. (68° F.).

The reaction solution was diluted with chloroform (5 ml). The solution was transferred to a separatory funnel and washed with distilled water, followed by 3% aqueous solution of sodium bicarbonate, and then with distilled water again. The chloroform layer was collected and dried over magnesium sulfate. The magnesium sulfate was filtered off via Hirsch filtration and rinsed with chloroform. The chloroform layer was removed under reduced pressure to give the crude product as a clear, colorless oil (824 mg).

Flash chromatography with 50:50 ethyl acetate:hexane as eluent on silica gel column yielded VC4 product (589 mg, 65.6% yield).

Further representative examples of compounds according to the present invention are as follows, each falling under the category of nicotinic acid glycerol esters of Structural Formula I, II, III, and/or IV, respectively Structural Formula I

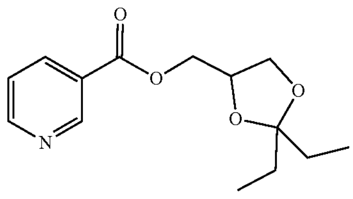

(2, 2-diethyl-1, 3-dioxolan-4-yl) methyl nicotinate

-continued

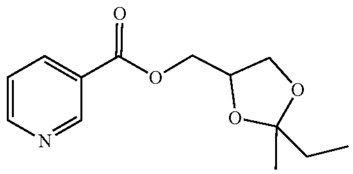

(2-ethyl-2-methyl-1, 3-dioxolan-4-yl) methyl nicotinate

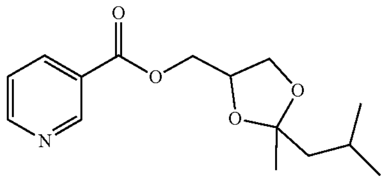

(2-isobutyl-2-methyl-1, 3-dioxolan-4-yl) methyl nicotinate

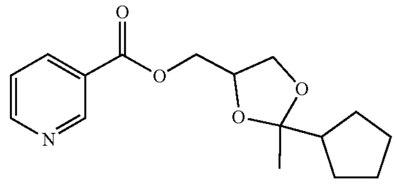

(2-cyclopentyl-2-methyl-1, 3-dioxolan-4-yl)methyl nicotinate

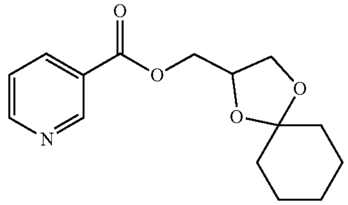

(1, 4-dioxaspiro[4.5]decan-2-yl)methyl nicotinate

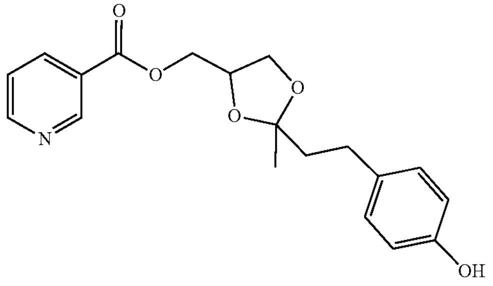

(2-(4-hydroxyphenethyl)-2-methyl-1, 3-dioxolan-4-yl) methyl nicotinate

Structural Formula II

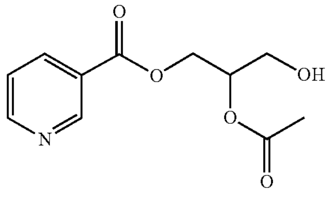

2-acetoxy-3-hydroxypropyl nicotinate

-continued

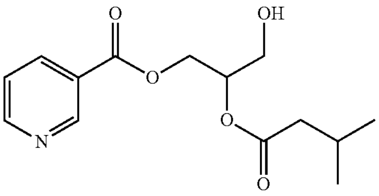

3-hydroxy-2-((3-methylbutanoyl)oxy) propyl nicotinate

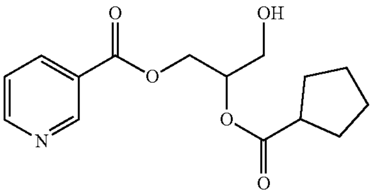

2-((cyclopentanecarbonyl)oxy)-3-hydroxypropyl nicotinate

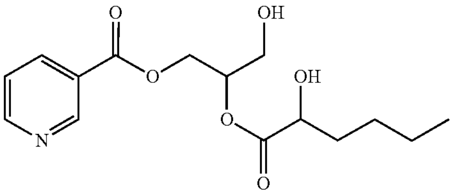

3-hydroxy-2-((2-hydroxyhexanoyl)oxy)propyl nicotinate

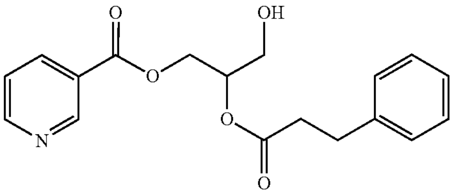

3-hydroxy-2-((3-phenylpropanoyl)oxy)propyl nicotinate

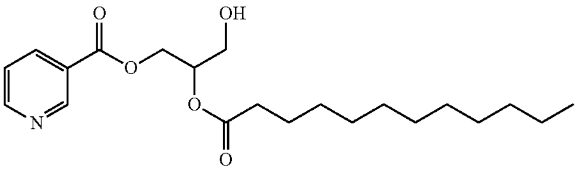

2-(dodecanoyloxy)-3-hydroxypropyl nicotinate

Structural Formula III

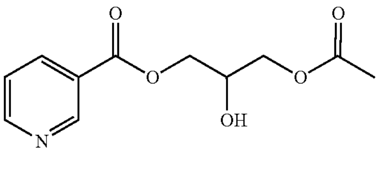

3-acetoxy-2-hydroxypropyl nicotinate

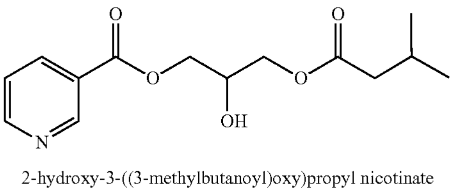

2-hydroxy-3-((3-methylbutanoyl)oxy)propyl nicotinate

-continued

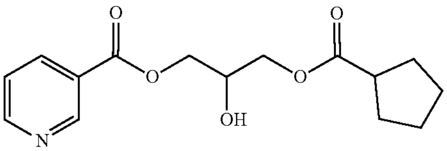

3-((cyclopentanecarbonyl)oxy)-2-hydroxypropyl nicotinate

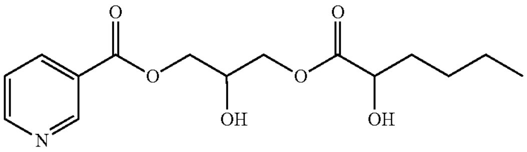

2-hydroxy-3-((2-hydroxyhexanoyl)oxy) propyl nicotinate

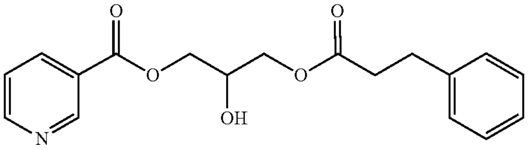

2-hydroxy-3-((3-phenylpropanoyl)oxy)propyl nicotinate

Structural Formula IV

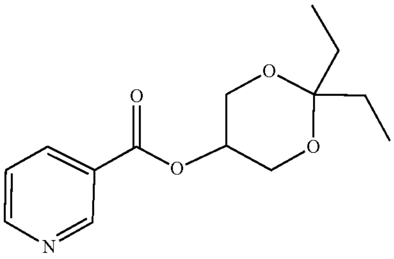

2, 2-diethyl-1, 3-dioxan-5-yl nicotinate

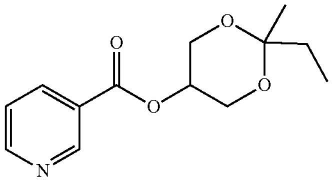

2-ethyl-2-methyl-1, 3-dioxan-5-yl nicotinate

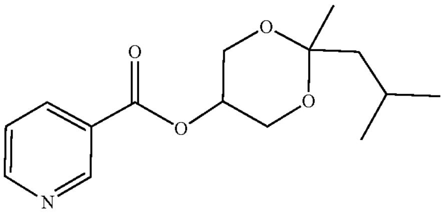

2-isobutyl-2-methyl-1, 3-dioxan-5-yl nicotinate

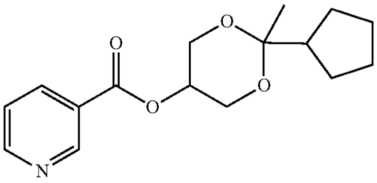

2-cyclopentyl-2-methyl-1, 3-dioxan-5-yl nicotinate

-continued

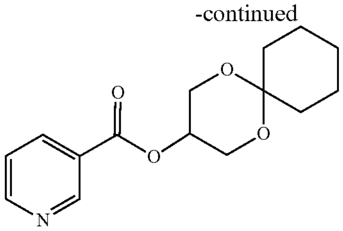

1, 5-dioxaspiro[5.5]undecan-3-yl nicotinate

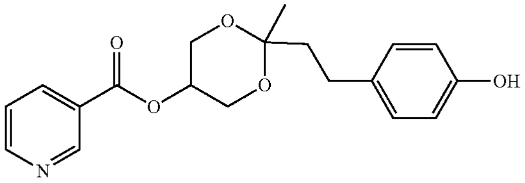

2-(4-hydroxyphenethyl-2-methyl-1, dioxn-5-yl nicotinate

Carrier

The compositions of this invention can have as cosmetically acceptable carriers non-polar liquids like oils. Alternatively, such non-polar liquids can be used as the oil phase when the composition is an emulsion.

When the compositions of the present invention are emulsions, they will typically include cosmetically acceptable carrier components in addition to non-polar liquid. Water is the most preferred additional carrier. Amounts of water may range from 1 to 99%, and preferably, from 5 to 90%, and most preferably, from 35 to 80%, and optimally, from 40 to 75% by weight, based on total weight of the composition and including all ranges subsumed therein. Ordinarily the compositions of this invention will be water and oil emulsions, most preferably, of the oil-in-water variety. Water-in-oil emulsions, and especially, those generally classified as water-in-oil and high internal phase emulsions are, however, an option. Illustrative examples of the high internal phase emulsions suitable to as carrier for this invention are described in commonly owned U.S. Patent Application Publication No. 2008/0311058 and U.S. Pat. No. 8,425,882, the disclosures of which are incorporated herein by reference.

Other cosmetically acceptable carriers suitable for use (with or without water) in this invention may include mineral oils, silicone oils, esters, and alcohols. Amounts of these materials may collectively range from 0.1 to 99%, and preferably, from 0.1 to 45%, and most preferably, from 1 to 20% by weight of the composition of this invention, including all ranges subsumed therein.

Silicone oils may be divided into the volatile and nonvolatile variety. The term “volatile” as used herein refers to those materials which have a measurable vapor pressure at ambient temperature. Volatile silicone oils are preferably chosen from cyclic or linear polydimethylsiloxanes containing from 3 to 9, and preferably, from 4 to 5 silicon atoms.

Linear volatile silicone materials generally have viscosities of less than 5 centistokes at 25° C. while cyclic materials typically have viscosities of less than about 10 centistokes.

Nonvolatile silicone oils useful as carrier material include polyalkyl siloxanes, polyalkylaryl siloxanes and polyether siloxane copolymers. The essentially non-volatile polyalkyl siloxanes useful herein include, for example, polydimethylsiloxanes (like dimethicone) with viscosities of from 5 to 100,000 centistokes at 25° C.

An often preferred silicone source is a cyclopentasiloxane and dimethiconol solution.

Among suitable esters are:

(I) Alkenyl or alkyl esters of fatty acids having 10 to 20 carbon atoms like isopropyl palmitate, isopropyl isostearate, isononyl isonanonoate, oleyl myristate, isopropyl myristate, oleyl stearate, and oleyl oleate;

(2) Ether-esters such as fatty acid esters of ethoxylated fatty alcohols;

(3) Polyhydric alcohol esters such as ethylene glycol mono- and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monooleate, polypropylene glycol 2000 mono stearate, ethoxylated propylene glycol monostearate, glyceryl mono- and di-fatty acid esters, polyglycerol poly-fatty esters, ethoxylated glyceryl mono-stearate, 1,3-butylene glycol monostearate, 1,3-butylene glycol distearate, polyoxyethylene polyol fatty acid ester, sorbitan fatty acid esters, and polyoxy-ethylene sorbitan fatty acid esters;

(4) Wax esters such as beeswax, spermaceti, myristyl myristate, stearyl stearate; and (5) Sterol esters, of which soya sterol and cholesterol fatty acid esters are examples thereof.

Often, oils such as caprylic capric triglyceride are preferred as carriers.

Emulsifiers may be present in the compositions of the present invention. Total concentration of the emulsifier may range from about 0.1 to 40%, and preferably, from 1 to 20%, and most preferably, from 1 to 5% by weight of the composition, including all ranges subsumed therein. The emulsifier may be selected from the group consisting of anionic, nonionic, cationic and amphoteric actives. Particularly preferred nonionic actives are those with a $C_{10}$-$C_{20}$ fatty alcohol or acid hydrophobe condensed with from about 2 to about 100 moles of ethylene oxide or propylene oxide per mole of hydrophobe; $C_2$-$C_{10}$ alkyl phenols condensed with from 2 to 20 moles of alkylene oxide; mono- and di-fatty acid esters of ethylene glycol; fatty acid monoglyceride; sorbitan, mono- and di-$C_8$-$C_{20}$ fatty acids; and polyoxyethylene sorbitan as well as combinations thereof. Alkyl polyglycosides and saccharide fatty amides (e.g. methyl gluconamides) are also suitable nonionic emulsifiers.

Preferred anionic emulsifiers include alkyl ether sulfate and sulfonates, alkyl sulfates and sulfonates, alkylbenzene sulfonates, alkyl and dialkyl sulfosuccinates, $C_8$-$C_{20}$acyl isethionates, $C_8$-$C_{20}$ alkyl ether phosphates, alkyl ether carboxylates and combinations thereof.

Cationic emulsifiers that may be used include, for example, almitamidopropyltrimonium chloride, distearyldimonium chloride and mixtures thereof. Useful amphoteric emulsifiers include cocoamidopropyl betaine, $C_{12}$-$C_{20}$ trialkyl betaines, sodium lauroamphoacetate, and sodium laurodiamphoacetate or a mixture thereof.

Other generally preferred emulsifiers include glyceryl stearate, glycol stearate, stearamide AMP, PEG-100 stearate, cetyl alcohol as well as emulsifying/thickening additives like hydroxyethylacrylate/sodium acryloyldimethyl taurates copolymer/squalane and mixtures thereof.

Composition

Preservatives can desirably be incorporated into the compositions of this invention to protect against the growth of potentially harmful microorganisms. Suitable traditional preservatives for compositions of this invention are alkyl esters of para-hydroxybenzoic acid. Other preservatives which have more recently come into use include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are iodopropynyl butyl carbamate, phenoxyethanol, 1,2-octanediol, ethylhexylglycerine, hexylene glycol, methyl paraben, propyl paraben, imidazolidinyl urea, sodium dehydroacetate and benzyl alcohol. The preservatives should be selected having regard for the use of the composition and possible incompatibilities between the preservatives and other ingredients in the emulsion. Preservatives are preferably employed in amounts ranging from 0.01% to 2% by weight of the composition, including all ranges subsumed therein. Combinations of 1,2-octanediol and phenoxyethanol, or iodopropynyl butyl carbamate and phenoxyethaol are preferred, with phenoxyethanol making up from 35 to 65% by weight of the total weight of the preservative combination with the phenoxyethanol.

Thickening agents may optionally be included in compositions of the present invention. Particularly useful are the polysaccharides. Examples include starches, natural/synthetic gums and cellulosics. Representative of the starches are chemically modified starches such as sodium hydroxypropyl starch phosphate and aluminum starch octenylsuccinate. Tapioca starch is often preferred. Suitable gums include xanthan, sclerotium, pectin, karaya, arabic, agar, guar, carrageenan, alginate and combinations thereof. Suitable cellulosics include hydroxypropyl cellulose, hydroxypropyl methylcellulose, ethylcellulose and sodium carboxy methylcellulose. Synthetic polymers are yet another class of effective thickening agent. This category includes crosslinked polyacrylates such as the Carbomers, polyacrylamides such as Sepigel 305 and taurate copolymers such as Simulgel EG and Arlstoflex AVC, the copolymers being identified by respective INCI nomenclature as Sodium Acrylate/Sodium Acryloyldimethyl Taurate and Acryloyl Dimethyltaurate/Vinyl Pyrrolidone Copolymer. Another preferred synthetic polymer suitable for thickening is an acrylate-based polymer made commercially available by Seppic and sold under the name Simulgel INS100.

Amounts of the thickener, when used, may range from 0.001 to 5%, and preferably, from 0.1 to 2%, and most preferably, from 0.2 to 0.5% by weight of the composition and including all ranges subsumed therein.

Fragrances, fixatives and abrasives may optionally be included in compositions of the present invention. Each of these substances may range from about 0.05 to about 5%, preferably between 0.1 and 3% by weight.

To enhance skin moisturization, cationic ammonium compounds may optionally be used in the compositions of this invention to enhance moisturization. Such compounds include salts of hydroxypropyltri ($C_1$-$C_3$ alkyl) ammonium mono-substituted-saccharide, salts of hydroxypropyltri ($C_1$-$C_3$ alkyl) ammonium mono-substituted polyols, dihydroxypropyltri ($C_1$-$C_3$ alkyl) ammonium salts, dihydroxypropyldi ($C_1$-$C_3$ alkyl) mono(hydroxyethyl) ammonium salts, guar hydroxypropyl trimonium salts, 2,3-dihydroxypropyl tri ($C_1$-$C_3$ alkyl or hydroxalkyl) ammonium salts or mixtures thereof. In a most preferred embodiment and when desired, the cationic ammonium compound employed in this invention is the quaternary ammonium compound 1,2-dihydroxypropyltrimonium chloride. If used, such compounds typically make up from 0.01 to 30%, and preferably, from 0.1 to 15% by weight of the composition.

When cationic ammonium compounds are used, additional preferred additives for use with the same are moisturizing agents such as substituted ureas like hydroxymethyl urea, hydroxyethyl urea, hydroxypropyl urea; bis(hydroxymethyl) urea; bis(hydroxyethyl)urea; bis(hydroxypropyl)urea; N, N'-dihydroxymethyl urea; N, N'-di-hydroxyethyl urea; N, N'-dihydroxypropyl urea; N, N, N'-trihydroxyethyl urea; tetra (hydroxymethyl)urea; tetra (hydroxyethyl)urea; tetra (hydroxypropyl)urea; N-methyl-N'-hydroxyethyl urea; N-ethyl-N, N—N'-hydroxyethyl urea; N-hydroxypropyl-N'-hydroxyethyl urea and N, N'-dimethyl-N-hydroxyethyl urea or mixtures thereof. Where the term hydroxypropyl appears, the meaning is generic for either 3-hydroxy-n-propyl, 2-hydroxy-n-propyl, 3-hydroxy-i-propyl or 2-hydroxy-i-propyl radicals. Most preferred is hydroxyethyl urea. The latter is available as a 50% aqueous liquid from the National Starch & Chemical Division of ICI under the trademark Hydrovance.

Amounts of substituted urea, when used, in the composition of this invention range from 0.01 to 20%, and preferably, from 0.5 to 15%, and most preferably, from 2 to 10% based on total weight of the composition and including all ranges subsumed therein.

Conventional humectants may be employed in the present invention as skin benefit agent and in addition to resorcinol and/or a derivative thereof. These are generally polyhydric alcohol type materials. Typical polyhydric alcohols include glycerol (i.e., glycerine or glycerin), propylene glycol, dipropylene glycol, polypropylene glycol, polyethylene glycol, sorbitol, hydroxypropyl sorbitol, hexylene glycol, 1,3-butylene glycol, isoprene glycol, 1,2,6-hexanetriol, ethoxylated glycerol, propoxylated glycerol and mixtures thereof. Most preferred is glycerin, propylene glycol or a mixture thereof. The amount of humectant employed may range anywhere from 0.5 to 20%, preferably between 1 and 15% by weight of the composition.

When cationic ammonium compound and substituted urea are used, in a most especially preferred embodiment at least from 1 to 15% glycerin is used, based on total weight of the composition and including all ranges subsumed therein.

Compositions of the present invention may optionally include vitamins, along with the actives and/or derivatives thereof according to the present invention. Illustrative vitamins are retinol (Vitamin A), Vitamin $B_2$, Vitamin $B_3$ (niacinamide), Vitamin $B_6$, Vitamin C, Vitamin E, Folic Acid and Biotin. Derivatives of the vitamins may also be employed. For instance, Vitamin C derivatives include ascorbyl tetraisopalmitate, magnesium ascorbyl phosphate and ascorbyl glycoside. Derivatives of Vitamin E include tocopheryl acetate, tocopheryl palmitate and tocopheryl linoleate. DL-panthenol and derivatives may also be used, and Vitamin D and K are also options. Total amount of optional vitamins when present in compositions according to the present invention may range from 0.0 to 10%, preferably from 0.001 to 1%, optimally from 0.01 to 0.5% by weight of the composition.

Optional Skin Benefit Agents

The compositions of the present invention can comprise in addition to NAEs and/or derivatives thereof, additional skin benefit agents (SBAs). It is preferred that NAEs and/or derivatives thereof make up at least 25% by weight, and preferably, at least 40 to 95% by weight, and most preferably, 100% by weight of the skin benefit agents. Optional skin benefit agents or additives may, if desired, be provided to make up the portion of the skin benefit agent that is not NAEs and/or a derivative thereof.

NRE

Optional skin benefit additives capable of increasing the AMP/ATP ratio can be used in combination with the nicotinic acid glycerol esters. These include but are not limited to 3-carbamoyl-1-((3R,4R,5R)-3,4-diacetoxy-5-(hydroxymethyl)tetrahydrofuran-2-yl)pyridin-1-ium trifluoromethanesulfonate ("JR1"), 1-((3R,4R,5R)-3,4-bis(butyryloxy)-5-(hydroxymethyl)tetrahydrofuran-2-yl)-3-carbamoylpyridin-1-ium trifluoromethanesulfonate ("JR2") and (3R,4R,5R)-2-(3-carbamoylpyridin-1(4H)-yl)-5-(hydroxymethyptetrahydrofuran-3,4-diyldiacetate ("J R3").

Additives JR1, JR2 and JR3 increase the AMP/ATP ratio over vehicle in fibroblast cells by 106, 150 and 235%, respectively.

The preferred NREs optionally used in accordance with the present invention are synthesized as follows, and their synthesis is representative of that for NREs in general.

Synthesis of JR1: 3-carbamoyl-1-((3R,4R,5R)-3,4-diacetoxy-5-(hydroxymethyl) tetrahydrofuran-2-yl) pyridin-1-ium trifluoromethanesulfonate 4-Methoxytrityl chloride (5.90 g, 19.1 mmol) was added to a solution of D-ribose (2.87 g, 19.1 mmol) in pyridine (35 ml) and the solution allowed to stir @ RT for 16 h. At this time, TLC showed the formation of a major product. The solvents were removed in vacuo @ 45° C. and the residue partitioned between ethyl acetate (100 ml) and 0.1N HCl (100 ml), the layers separated and the organic layer dried with sodium sulfate, filtered and the solvents removed to give an orange gel. The product was purified by flash chromatography on silica gel 4% methanol in dichloromethane to give pure product (3R,4S,5R)-5-(((4-methoxyphenyl) diphenylmethoxy)methyl)tetrahydrofuran-2,3,4-triol (JR1A) as a colorless gel (5.1 g, 63%). Acetic anhydride (1.63 ml, 17.2 mmol) was added to JR1A (1.27 g, 3.02 mmol) in pyridine (8 ml) and the solution allowed to stir @ RT for 16 h. At this time, TLC showed the formation of a major product. The mixture was partitioned between ethyl acetate (50 ml) and saturated sodium bicarbonate (50 ml), the layers separated and the organic layer filtered through sodium sulfate and the solvents removed to give a pale yellow gel (1.83 g). The product was purified by flash chromatography on silica gel using 30% ethyl acetate in hexane to give pure product (3R,4R,5R)-5-(((4-methoxyphenyl)diphenylmethoxy)methyl)tetrahydrofuran-2,3,4-triyl triacetate (JR1B) as a colorless gel (1.12 g, 68%). JR1B (1.1 g, 2.0 mmoL) was dissolved in 80% aqueous acetic acid (18 ml) and the solution allowed to sit @ RT for 6 h. At this time, TLC showed the clean formation of a major product. Saturated sodium bicarbonate (100 ml) was slowly added, followed by ethyl acetate (100 ml) and the mixture vigorously shaken. The layers were separated and the organic layer filtered through sodium sulfate and the solvents removed to give a colorless gel. The product was purified by flash chromatography on silica gel using 55% ethyl acetate in hexane to give pure product (3R,4R,5R)-5-(hydroxymethyl) tetrahydrofuran-2,3,4-triyl triacetate (JR1C) as a colorless gel (476 mg, 86%). Trimethylsilyl trifluoromethanesulfonate (324 uL, 1.8 mmol) was added to a solution of JR1C (450 mg, 1.6 mmol) and N-(trimethylsilyl) nicotinamide (316 mg, 1.6 mmol) in 1,2-dichloroethane (3.5 ml) @ 10° C. and allowed to warm up to RT over 3 hr. At this time, TLC showed the clean formation of product. Methanol (1 ml) was added and stirred for 30 min and the solvents were removed in vacuo between 40-45° C. to give a yellow-orange oil. The product was purified by flash chromatography on silica gel using 0 to 10% methanol in dichloromethane gradient, followed by 10% methanol in dichloromethane isocratic to give pure product JR1 as a colorless foam (440 mg, 55%). $^{1}$H NMR and LC/MS confirmed product identity and HPLC showed 98% purity.

Synthesis of JR2: 1-((3R,4R,5R)-3,4-bis(butyryloxy)-5-(hydroxymethyl)tetrahydrofuran-2-yl)-3-carbamoylpyridin-1-ium trifluoromethanesulfonate Butyric anhydride (2.81 ml, 17.2 mmol) was added to JR1A (1.27 g, 3.02 mmol) in pyridine (8 ml) and the solution allowed to stir @ RT for 16 h. At this time, TLC showed the formation of a major product. The mixture was partitioned between ethyl acetate (50 ml) and saturated sodium bicarbonate (50 ml), the layers separated and the organic layer filtered through sodium sulfate and the solvents removed to give a pale yellow gel (1.83 g). The product was purified by flash chromatography on silica gel using 10% ethyl acetate in hexane to give pure product (3R,4R,5R)-5-(((4-methoxyphenyl)diphenylmethoxy)methyl)tetrahydrofuran-2,3,4-triyl tributyrate (JR2B) as a colorless gel (1.99 g, 100%). JR2B (1.97 g, 3.1 mmoL) was dissolved in 80% aqueous acetic acid (28 ml) and the solution allowed to sit @ RT for 6 h. At this time, TLC showed the clean formation of a major product. Saturated sodium bicarbonate (100 ml) was slowly added, followed by ethyl acetate (100 ml) and the mixture vigorously shaken. The layers were separated and the organic layer filtered through sodium sulfate and the solvents removed to give a colorless gel. The product was purified by flash chromatography on silica gel using 30% ethyl acetate in hexane to give pure product (3R,4R,5R)-5-(hydroxymethyl) tetrahydrofuran-2,3,4-triyl tributyrate (JR2C) as a colorless gel (628 mg, 55%). Trimethylsilyl trifluoromethanesulfonate (331 uL, 1.9 mmol) was added to a solution of JR2C (600 mg, 1.7 mmol) and N-(trimethylsilyl) nicotinamide (323 mg, 1.7 mmol) in 1,2-dichloroethane (3.7 ml) @ 10° C. and allowed to warm up to RT over 1 hr. At this time, TLC showed the clean formation of product. The reaction mixture was diluted with 15% isopropanol in chloroform (5 ml) and washed with 0.15N HCl saturated with sodium chloride (2×10 ml). The aqueous layers were back extracted with ethyl acetate (1×20 ml) and the combined organic layers filtered through sodium sulfate and the solvents removed to give a yellow oil. The product was purified by flash chromatography on silica gel using 10% methanol in dichloromethane gradient to give pure product JR2 as a colorless gel (451 mg, 50%). $^{1}$H NMR and LC/MS confirmed product identity and HPLC showed 95% purity.

Synthesis of JR3: (3R,4R,5R)-2-(3-carbamoylpyridin-1(4H)-yl)-5-(hydroxymethyl) tetrahydrofuran-3,4-diyl diacetate JR1 (200 mg, 0.4 mmol) was dissolved in degassed deionized water (1 ml) and slowly added to a mixture of sodium dithionite (142 mg, 0.8 mmol) and sodium bicarbonate (172 mg, 2.0 mmol) in water (1 ml) and the solution diluted with degassed deionized water (1 ml). After vigorous stirring for 40 min, TLC showed the formation of a major product. The reaction was diluted with 15% isopropanol in chloroform (8 ml), saturated sodium chloride (8 ml) was added and the mixture shaken. The layers were separated and the organic layer was filtered through a bed of sodium sulfate. The aqueous layer was further extracted with 15% isopropanol in chloroform (2×8 ml) and the combined organic layers evaporated in vacuo @ 40° C. to give a pale yellow foam (107 mg). The product was purified by flash chromatography on silica gel using 6% methanol in dichloromethane to give JR3 as a pale yellow foamy solid (60 mg, 43%). $^{1}H$ NMR and LC/MS confirmed product identity and HPLC showed 97% purity.

Other optional additives suitable for use in this invention include alpha- and/or beta-hydroxyacids, 12-hydroxystearic acid, petroselinic acid, conjugated linoleic acid, creatine, creatinine, retinoid boosters (e.g., climbazole, bibonazole, farnesole, glycyrrchetinic acid, ursolic acid, geranyl geraniol, oleyl betaine, hexanoyl sphingosine) mixtures thereof or the like. Such additives, when used, collectively make up from about 0.001 to about 12% by weight of the composition.

Desquamation promoters may be present. Illustrative are the alpha-hydroxycarboxylic acids, beta-hydroxycarboxylic acids. The term "acid" is meant to include not only the free acid but also salts and $C_1$-$C_{30}$ alkyl or aryl esters thereof and lactones generated from removal of water to form cyclic or linear lactone structures. Representative acids are glycolic and its derivatives, lactic and malic acids. Salicylic acid is representative of the beta-hydroxycarboxylic acids. Amounts of these materials when present may range from 0.01 to 15% by weight of the composition of this invention.

A variety of herbal extracts may optionally be included in compositions of this invention. The extracts may either be water soluble or water-insoluble carried in a solvent which respectively is hydrophilic or hydrophobic. Water and ethanol are the preferred extract solvents. Illustrative extracts include those from green tea, yarrow, chamomile, licorice, aloe vera, grape seed, citrus unshui, wasabi, willow bark, sage, thyme and rosemary.

Also optionally suitable for use include materials like chelators (e.g., EDTA), opacifiers (like $TiO_2$, particle size from 50 to 1200 nm, and preferably, 50 to 350 nm), $C_{8-22}$ fatty acid substituted saccharides, lipoic acid, retinoxytrimethylsilane (available from Clariant Corp. under the SilCare IM-75 trademark), dehydroepiandrosterone (DHEA) and combinations thereof. Ceramides (including Ceramide I, Ceramide 3, Ceramide 36 and Ceramide 6) as well as pseudoceramides may also be useful. Amounts of these materials may range from 0.000001 to 10%, preferably from 0.0001 to 1% by weight of the composition of this invention.

Sunscreen actives may also be included in compositions of the present invention. Particularly preferred are such materials as ethylhexyl p-methoxycinnamate, available as Parsol MCX, Avobenzene, available as Parsol 1789 and benzophenone-3, also known as Oxybenzone. Inorganic sunscreen actives may be employed such as microfine titanium dioxide, octocrylene zinc oxide, polyethylene and various other polymers.

Amounts of the sunscreen agents when present may generally range from 0.1 to 30%, preferably from 0.5 to 20%, optimally from 0.75 to 10% by weight.

Conventional buffers/pH modifiers may be used. These include commonly employed additives like sodium hydroxide, potassium hydroxide, hydrochloric acid, citric acid and citrate/citric acid buffers. In an especially preferred embodiment, the pH of the composition of this invention is from 4 to 8, and preferably, from 4.25 to 7.75, and most preferably, from 6 to 7.5, including all ranges subsumed therein.

The composition of the present invention preferably is a leave-on skin lotion, cream, shampoo, conditioner, shower gel, antiperspirant, deodorant, depilatory, shave cream or toilet bar.

Packaging

A wide variety of packaging can be employed to store and deliver the composition with stable NAEs of this invention. Packaging is often dependent upon the type of personal care end-use. For instance, leave-on skin lotions and creams, shampoos, conditioners and shower gels generally employ plastic containers with an opening at a dispensing end covered by a closure. Typical closures are screw-caps, nonaerosol pumps and flip-top hinged lids. Packaging for antiperspirants, deodorants and depilatories may involve a container with a roll-on ball on a dispensing end. Alternatively, these types of personal care products may be delivered in a stick composition formulation in a container with propel repel mechanism where the stick moves on a platform towards a dispensing orifice. Metallic cans pressurized by a propellant and having a spray nozzle serve as packaging for antiperspirants, shave creams and other personal care products. Toilette bars may have packaging constituted by a cellulosic or plastic wrapper or within a cardboard box or even encompassed by a shrink wrap plastic film.

The following examples are provided to facilitate an understanding of the present invention. The examples are not intended to limit the scope of the claims.

EXAMPLES

Example 1

Solubility

The purpose of this experiment was to compare water solubility of various nicotinic acid ester compounds, which is a required characteristic for formulation and delivery.

Log P of the various nicotinic acid ester compounds was calculated. The higher the Log P of a molecule, the more lipophilic and less water soluble the molecule.

TABLE 3

| LogP | | |
|---|---|---|
| Test Sample | Calculated Log P | Predicted Solubility |
| Myristyl nicotinate | 7.6 * | Lipophilic/ water insoluble |
| VC1 | 1.45 | Water soluble |
| VC2 | −0.53 | Water soluble |
| VC3 | 4.09 | Water soluble |
| VC4 | 1.45 | Water soluble |

(* U.S. Pat. No. 6,677,361)

As can be seen from the data in the Table above, Myristyl nicotinate is water insoluble; it is a very lipophilic molecule, having a high log P, so it is water insoluble and difficult to formulate in a cosmetic composition. Myristil nicotinate also has a greasy feel.

In contrast, the calculated Log P of NAE derivative compounds VC1, VC2 and VC4 are between log P<5.8 and Log P>−1. The NAE derivative compounds VC1, VC2 and VC4 are relatively more water soluble than Myristyl nicotinate. Therefore, the compounds according to the present invention are predicted to have better dermal delivery than myristyl nicotinate.

Example 2

Effect of NAEs on AMP/ATP Ratio in Fibroblast Cells

The experiments in this Example 2 were conducted in the following manner.

Method for Treatment of Fibroblasts with Bioenergetic Compounds

Human dermal fibroblasts F5140616B1 (MatTek Corporation, Ashland, Mass.) were derived from a 40-year old female donor and cultured in DMEM media (ThermoFisher Cat #31053-036) supplemented with FBS (Hyclone/Fisher Scientific Cat #SH30007103), glutamine (ThermoFisher Cat #35050-61) and sodium pyruvate (ThermoFisher Cat #11360-070). At the third passage, the cells were detached from the culture vessels using Trypsin/EDTA (T/E) solution (0.25 mg/mL) (Lonza Cat #CC-5012) and used for experimentation.

Cells were treated with the compounds every other day for a total of 6 days. Treatment involved removal of the spent media+compounds and replenishment with fresh media+compounds. At the end of the experiment, the cells were detached from the culture vessels using the standard procedure outlined above. The cells were centrifuged and then washed 1× with Dulbecco's PBS with no calcium or magnesium (ThermoFisher Cat #14190144) and then accurate cell counts were taken using a Scepter cell counter (EMD Millipore). The cells were then split equally into 2 Eppendorf tubes, and centrifuged. Excess PBS was then removed from the resulting cell pellets. The pellets were then immediately frozen on dry ice and sent to an external laboratory for analysis of metabolites by LC/MS.

The data is presented in the Table below.

TABLE 4

| AMP/ATP Ratio Data | | |
|---|---|---|
| Test Sample | AMP/ATP Ratio | Increase Over Vehicle |
| Vehicle (ethanol) | 367 | — |
| Nicotinamide (500 uM) | 529 | 44% |
| VC1 (500 uM) | 1010 | 175% |
| VC4 (500 uM) | 941 | 156% |
| Optional Skin Benefit Agents | | — |
| JR1 (500 uM) | 756 | 106% |
| JR2 (500 uM) | 919 | 150% |
| JR3 (500 uM) | 1231 | 235% |

The data demonstrates that Nicotinamide at a dose of 500 uM showed somewhat elevated levels of AMP/ATP ratio over control vehicle (which can signal AMPK).

The results show that Compounds VC1 and VC4 at doses of 500 uM showed significantly elevated levels of AMP/ATP ratio over both, control vehicle and nicotinamide.

The increase in the levels of AMP/ATP ratio by compounds VC1 and VC2 leads to increased cellular energy available to improve and maintain a healthy skin appearance. Additives JR1, JR2 and JR3 increase the AMP/ATP ratio over vehicle in fibroblast cells by 106, 150 and 235%, respectively.

Example 3

Personal care formulations according to the present invention are illustrated in the Tables below. All numbers in Tables represent weight % in the composition.

TABLE 5A

| Oil-in-water formulations, lotions, and creams | | | | | |
|---|---|---|---|---|---|
| | OW-1 | OW-2 | OW-3 | OW-4 | OW-5 |
| Water | To 100 | To 100 | To 100 | To 100 | To 100 |
| Glycerine | 0-40 | 1-40 | 1-5 | 1-10 | 1-40 |
| Propylene glycol | 0-5 | | 0-5 | | |
| Butylene glycol | 0-5 | | 0-5 | 0-5 | |
| Carbomer | 0-2 | 0.03-1 | | | |
| Ammonium Acryloyl dimethyl taurate/VP copolymer | 0-1 | | 0.03-1 | | 0.01-1 |
| Styrene/Acrylates copolymer | 0-1 | | 0.01-1 | | |
| Xanthan Gum | 0-1 | | | | 0.01-1 |
| EDTA | 0.01-0.01 | 0.01-0.01 | 0.01-1 | 0.01-1 | 0.01-1 |
| Preservative | 0.02-2 | 0.02-2 | 0.02-2 | 0.02-2 | 0.02-2 |
| Titanium oxide | 0-10 | 0.01-10 | 0.01-10 | 0.01-10 | 0.01-10 |
| Colorant/Pigment | 0-5 | 0-5 | 0-5 | 0-5 | 0-5 |
| Triethanol amine/ Sodium Hydroxide/ potassium Hydroxide | 0-3 | 0.01-3 | 0.01-3 | 0.01-3 | 0.01-3 |
| Stearic acid | 0-5 | 0.01-5 | 0.01-5 | 0.01-5 | 0.01-5 |
| Isopropyl Myristate | 0-10 | 0.01-10 | | | |
| Capric/Caprylic Triglyceride | 0-10 | 0.01-10 | | | |
| C12-C15 alkyl benzoate | 0-10 | | | | 0.01-10 |
| Mineral oil | 0-10 | | | 0.01-10 | |
| Glyceryl stearate | 0-5 | 0.01-5 | | | |
| Steareth-2 | 0-5 | | 0.01-5 | | 0.01-5 |
| Steareth-21 | 0-5 | | 0.01-5 | | |
| Peg100 Stearate | 0-5 | | | 0.01-2 | 0.01-5 |
| Potassium Cetyl Phosphate | 0-5 | | | 0.01-2 | |
| Tween20 | 0-5 | | | | 0.01-5 |
| Cetyl alcohol | 0-4 | 0.01-4 | | 0.01-4 | |

TABLE 5A-continued

| Oil-in-water formulations, lotions, and creams | | | | | |
|---|---|---|---|---|---|
| | OW-1 | OW-2 | OW-3 | OW-4 | OW-5 |
| Dicaprylyl carbonate | 0-5 | | 0.01-5 | | |
| UVA and/or UVB Sunscreens | 0-6 | 0.01-6 | | 0.01-10 | 0.01-10 |
| Silicones | 0-15 | 0.01-10 | 0.01-15 | | |
| Fragrance | 0-2 | 0-2 | 0-2 | 0-2 | 0-2 |
| VC1 | | 0.01-10 | 0.01-10 | 0.01-10 | 0.01-10 |
| VC2 | 0.01-10 | 0.01-10 | | 0.01-10 | 0.01-10 |
| VC3 | 0.01-10 | 0.01-10 | 0.01-10 | 0.01-10 | |
| VC4 | 0.001-2 | 0.001-2 | 0.001-2 | 0.001-2 | 0.001-2 |

TABLE 5B

| Water-in-oil topical lotions or creams | | | | |
|---|---|---|---|---|
| | WO-1 | WO-2 | WO-3 | WO-4 |
| Water | To 100 | To 100 | To 100 | To 100 |
| Glycerine | 0-70 | 1-70 | 1-70 | |
| Propylene glycol | 0-5 | | | 0.01-5 |
| Butylene glycol | 0-5 | | 0.01-5 | 0.01-5 |
| Disteardimonium Hectorite | 0.01-1 | 0.01-1 | | |
| EDTA | 0.01-.01 | 0.01-1 | 0.01-1 | 0.01-1 |
| Preservative | 0.02-2 | 0.02-2 | 0.02-2 | 0.02-2 |
| TiO2 | 0-10 | 0.01-10 | 0.01-10 | 0.01-10 |
| Colorant/pigment | 0-5 | 0-5 | 0-5 | 0-5 |
| TEA/Sodium Hydroxide/ potassium Hydroxide | 0-3 | 0.01-3 | 0.01-3 | 0.01-3 |
| Stearic acid | 0-5 | 0.01-5 | | |
| Isopropyl Myristate | 0-10 | | | |
| Capric/Caprylic Triglyceride | 0-10 | | 0.01-10 | |
| C12-C15 alkyl benzoate | 0-10 | | | 0.01-10 |
| Mineral oil | 0-10 | | | |
| Glyceryl stearate | 0-5 | | | |
| Dimethicone copolyol | 0-5 | 0.01-5 | 0.01-5 | |
| Cetyl PEG/PPG-10/1 Dimethicone | 0-5 | | | 0.01-5 |
| Steareth-2 | 0-2 | | | |
| Sucrose Distearate | 0-2 | 0.01-2 | | |
| Cetyl alcohol | 0-2 | 0.01-2 | 0.01-2 | |
| UVA and/or UVB Sunscreens | 0-6 | 0.01-6 | 0.01-10 | 0.01-10 |
| Dimethicone | 0-10 | | 0.01-10 | 0.01-10 |
| Cyclomethicone | 0-40 | 0.01-40 | | 0.01-10 |
| Caprylyl methicone | 0-10 | 0.01-10 | | 0.01-10 |
| Dimethicone crosspolymer | 0-90 | 0.01-90 | 0.01-90 | |
| C30-C45 alkyl cetearyl dimethicone crosspolymer | | | | 0.01-90 |
| Glycolic acid | 0-10 | 0.01-10 | | |
| KCl | 0-5 | 0.01-5 | 0.01-5 | 0.01-5 |
| Fragrance | 0-2 | 0-2 | 0-2 | 0-2 |
| VC1 | 0.01-10 | 0.01-10 | 0.01-10 | 0.01-10 |
| VC2 | 0.01-10 | 0.01-10 | 0.01-10 | 0.01-10 |
| VC3 | 0.01-10 | 0.01-10 | 0.01-10 | 0.01-10 |
| VC4 | 0.001-2 | 0.001-2 | 0.001-2 | 0.001-2 |

TABLE 5C

| Vanishing Creams | | | | |
|---|---|---|---|---|
| | VC1 | VC2 | VC3 | VC4 |
| Water | To 100 | To 100 | To 100 | To 100 |
| Glycerine | 0-5 | 0.01-5 | 0.01-5 | |
| EDTA | 0.01-.01 | 0.01-.01 | 0.01-.01 | 0.01-.01 |

TABLE 5C-continued

| Vanishing Creams | | | | |
|---|---|---|---|---|
| | VC1 | VC2 | VC3 | VC4 |
| Preservative | 0.02-2 | 0.02-2 | 0.02-2 | 0.02-2 |
| TiO2 | 0.01-10 | 0.01-10 | 0.01-10 | 0.01-10 |
| Colorant/pigment | 0-5 | 0.01-5 | 0.01-5 | |
| EA/Sodium Hydroxide/ potassium Hydroxide | 0-3 | 0.01-3 | 0.01-3 | 0.01-3 |
| Stearic acid | 0-30 | 0.01-30 | 0.01-30 | 0.01-30 |
| Isopropyl Myristate | 0-5 | 0.01-10 | 0.01-10 | |
| C12-C15 alkyl benzoate | 0-5 | | | 0.01-10 |
| Brij 35 | 0-5 | 0.01-5 | | |
| Tween40 | 0-5 | | | 0.01-5 |
| Cetyl alcohol | 0-2 | 0.01-2 | 0.01-2 | |
| Ethyl hexyl methoxycinnamate | 0-6 | 0.01-6 | 0.01-6 | |
| Butyl Methoxydi-benzoylmethane | 0-3 | 0.01-3 | 0.01-3 | 0.01-3 |
| Ensulizole | 0-4 | | | 0.01-4 |
| Octisalate | 0-5 | | | 0.01-5 |
| Octocrylene | 0-10 | | 0.01-10 | 0.01-10 |
| Dimethicone | 0-5 | 0.01-5 | | |
| Cyclomethicone | 0-5 | | | 0.01-5 |
| Dimethicone crosspolymer | 0-4 | | | 0.01-4 |
| Hydroxystearic acid | 0-5 | 0.01-5 | 0.01-5 | 0.01-5 |
| Fragrance | 0-2 | 0-2 | 0-2 | 0-2 |
| VC1 | 0.01-3 | 0.01-3 | 0.01-3 | 0.01-3 |
| VC2 | 0.01-3 | 0.01-3 | 0.01-3 | 0.01-3 |
| VC3 | 0.01-3 | 0.01-3 | 0.01-3 | 0.01-3 |
| VC4 | 0.001-3 | 0.001-3 | 0.001-3 | 0.001-3 |

What is claimed is:

1. A nicotinic acid glycerol ester compound consisting of:

a. Structural Formula IV

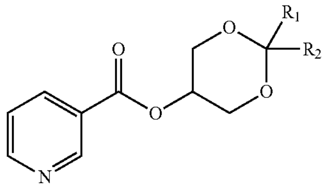

wherein R1 and R2 are independently C1-C5 linear, branched or cyclic alkyl; saturated or unsaturated; with or without a heteroatom; including salts thereof.

2. The compound according to claim 1 characterized in that said compound has a log P that is greater than −1 and less than 5.8.

3. The compound according to claim 1 characterized in that said compound has effectiveness as AMPK activator or modulator.

4. The compound according to claim 1 characterized in that said compound has effectiveness to increase cellular AMP/ATP ratio over vehicle in skin fibroblast cells.

5. The compound of Structural Formula IV according to claim 1 in a mixture with one or more further nicotinic acid glycerol ester compound(s) selected from the group consisting of:

(a) Structural Formula I

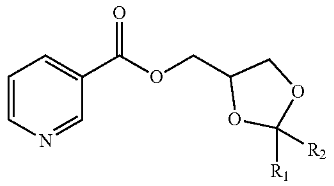

wherein R1 and R2 are independently C1-C5 linear, branched or cyclic alkyl; saturated or unsaturated; with or without a heteroatom (like —OH); including salts thereof;

(b) Structural Formula II

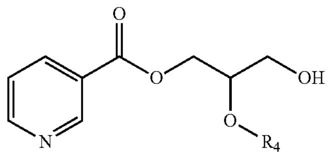

wherein R4 is H or O═C—X2, where X2=C1-C11 linear, branched or cyclic alkyl; saturated or unsaturated; with or without a heteroatom (like —OH); including salts thereof, (c) Structural Formula III

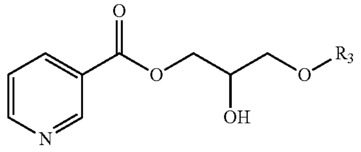

wherein R3 is H or O═C—X (glycerol ester), where X═C1-C12 linear, branched or cyclic alkyl; saturated or unsaturated; with or without a heteroatom (like —OH); including salts thereof;

characterized in that said compounds have a log P that is greater than −1 and less than 5.8;

and further characterized in that said compound(s) have effectiveness as AMPK activator or modulator.

6. The compound(s) according to claim 1 wherein the compound(s) are selected from the group consisting of:

Structural Formula VC1

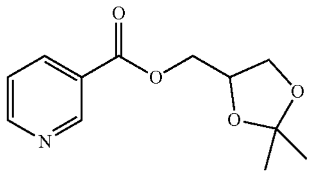 [SMILES: CC1(C)OCC(COC(=O)c2cccnc2)O1]

Structural Formula VC2

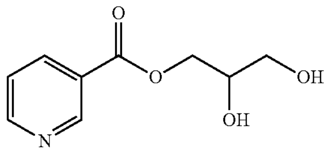 [SMILES: O=C(OCC(O)CO)c1cccnc1]

Structural Formula VC3

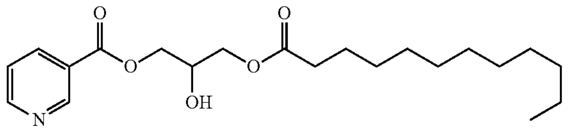 [SMILES: CCCCCCCCCCCC(=O)OCC(O)COC(=O)c1cccnc1]

Structural Formula VC4

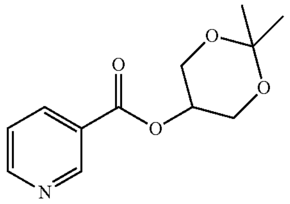 [SMILES: CC1(C)OCC(OC(=O)c2cccnc2)CO1]

and mixtures thereof.

7. A topical personal care composition comprising:

(a) a nicotinic acid glycerol ester compound according to claim 1;

(b) an optional skin benefit agent; and (c) a cosmetically acceptable carrier.

8. The topical personal care composition according to claim 7 wherein the nicotinic acid glycerol ester compound is present at a concentration from 0.001 to 10% by weight of the composition.

9. The topical personal care composition according to claim 7 wherein the composition is not an emulsion.

10. The topical personal care composition according to claim 7 wherein the composition is an emulsion.

11. The topical personal care composition according to claim 7 wherein the composition further comprises retinoic acid, creatine, 1,2-octanediol, sunscreen, conjugated linoleic acid, hydroxyl acid, niacinamide, 12-hydroxystearic acid, phenoxyethanol or a mixture thereof.

12. The topical personal care composition according to claim 10 wherein the emulsion is an oil-in-water emulsion.

13. A method according to claim 12, wherein said optional skin benefit agent is selected from the group consisting of 3-carbamoyl-1-((3R,4R,5R)-3,4-diacetoxy-5-(hydroxymethyl)tetrahydrofuran-2-yl)pyridin-1-ium trifluoromethanesulfonate ("JR1"), 1-((3R,4R,5R)-3,4-bis(butyryloxy)-5-(hydroxymethyl)tetrahydrofuran-2-yl)-3-carbamoylpyridin-1-ium trifluoromethanesulfonate ("JR2") and (3R,4R,5R)-2-(3-carbamoylpyridin-1(4H)-yl)-5-(hydroxymethyl) tetrahydrofuran-3,4-diyl diacetate ("JR3"), and a mixture thereof.

14. The topical personal care composition according to claim 10 wherein the emulsion is an oil-in-water emulsion.

* * * * *

UNITED STATES PATENT AND TRADEMARK OFFICE

CERTIFICATE OF CORRECTION

PATENT NO. : 11,767,314 B2
APPLICATION NO. : 17/288173
DATED : September 26, 2023
INVENTOR(S) : Van Au et al.

It is certified that error appears in the above-identified patent and that said Letters Patent is hereby corrected as shown below:

In the Claims

Claim 12
Column 32, Lines 64-65 “The topical personal care composition according to claim 10 wherein the emulsion is an oil-in-water emulsion.” should read --A method for activating cellular AMPK using a nicotinic acid glycerol ester compound according to claim 1 in a composition, said method comprising a step of topically applying to skin the composition comprising the nicotinic acid glycerol ester compound with an optional skin benefit agent in a suitable vehicle.--

Signed and Sealed this
Nineteenth Day of December, 2023

Katherine Kelly Vidal

Katherine Kelly Vidal
*Director of the United States Patent and Trademark Office*